(12) United States Patent
Lin et al.

(10) Patent No.: US 9,345,434 B2
(45) Date of Patent: May 24, 2016

(54) PHYSIOLOGICAL SIGNAL MEASUREMENT APPARATUS CAPABLE OF AUTOMATICALLY ADJUSTING A MEASURE POSITION AND METHOD OF UTILIZING THE APPARATUS

(71) Applicant: National Taiwan University of Science and Technology, Taipei (TW)

(72) Inventors: Yuan-Hsiang Lin, Taipei (TW); Chong-Rong Wu, Taipei (TW)

(73) Assignee: National Taiwan University of Science and Technology (TW)

( * ) Notice: Subject to any disclaimer, the term of this patent is extended or adjusted under 35 U.S.C. 154(b) by 70 days.

(21) Appl. No.: 14/311,969

(22) Filed: Jun. 23, 2014

(65) Prior Publication Data

US 2015/0099985 A1    Apr. 9, 2015

(30) Foreign Application Priority Data

Oct. 3, 2013    (TW) .............................. 102135908 A

(51) Int. Cl.
| | |
|---|---|
| *A61B 5/02* | (2006.01) |
| *A61B 5/00* | (2006.01) |
| *A61B 5/0402* | (2006.01) |
| *A61B 5/026* | (2006.01) |
| *A61B 5/024* | (2006.01) |

(52) U.S. Cl.
CPC .............. *A61B 5/6843* (2013.01); *A61B 5/0402* (2013.01); *A61B 5/6891* (2013.01); *A61B 5/6893* (2013.01); *A61B 5/02* (2013.01); *A61B 5/026* (2013.01); *A61B 5/02416* (2013.01)

(58) Field of Classification Search
CPC ...... A61B 5/02; A61B 5/02416; A61B 5/026; A61B 5/0402; A61B 5/6843; A61B 5/6891; A61B 5/6893
See application file for complete search history.

(56) References Cited

U.S. PATENT DOCUMENTS

| | | | |
|---|---|---|---|
| 8,116,838 B2 * | 2/2012 | Gaspard ............... | A61B 5/0075 600/322 |
| 2006/0184048 A1 * | 8/2006 | Saadat ................. | A61B 1/0008 600/478 |
| 2013/0172759 A1 * | 7/2013 | Melker ............... | A61M 39/281 600/476 |
| 2013/0324860 A1 * | 12/2013 | Borgos ................... | A61B 5/022 600/480 |

\* cited by examiner

*Primary Examiner* — Mark Remaly
(74) *Attorney, Agent, or Firm* — Bacon & Thomas, PLLC

(57) ABSTRACT

A physiological signal measurement apparatus is capable of automatically adjusting a measure position and suitable for installed on a support element to measure a physiological signal of a user. The physiological signal measurement apparatus includes a movable element, a physiological signal sensing element, a pressure sensing unit and a microcontroller unit. The movable element has a first pressure. The user exerts a second pressure on the physiological signal sensing element, and exerts a third pressure on the support element. The pressure sensing unit senses the first pressure, the second pressure and the third pressure to generate a first pressure signal, a second pressure signal and a third pressure signal. The microcontroller unit receives the physiological signals and the pressure signals, and controls the movable element by the pressure signals and the physiological signals, in order to increase the quality of signal measurement.

7 Claims, 5 Drawing Sheets

PHYSIOLOGICAL SIGNAL MEASUREMENT APPARATUS CAPABLE OF AUTOMATICALLY ADJUSTING A MEASURE POSITION AND METHOD OF UTILIZING THE APPARATUS

BACKGROUND OF THE INVENTION (1) Field of the Invention

The invention relates to a physiological signal measurement apparatus, and especially relates to a physiological signal measurement apparatus capable of automatically adjusting a measure position and method of utilizing the apparatus.

(2) Description of the Prior Art

For the convenience of monitoring of Electrocardiography (ECG) signal, it has developed a indirect-contact ECG signal measurement manner. The manner is that making the sensing electrodes install on the seat, the users do not have to take off his or her clothes, just lying on the seat, then the users can measure the ECG signal.

The users must lie on a chair to measure the ECG signal in the above manner. However, when the user's body moving or can not be in contact with the sensing electrode, it will generate a lot interference or be unable to measure a stable ECG signal, so the ECG signal will not be recognized and analyzed. There has been research team, using principal component analysis algorithm to reduce the interference, and apply in traffic measurement practically, but the ECG signal is still affected by the movement of the users easily, such as the moving interference generated by the significant body movement of the users. The ECG signal will not be measured due to the users away from the seat or bad contact with the electrode. Therefore, to overcome the moving interference and enhance the quality of signal is an important research issue.

SUMMARY OF THE INVENTION

Accordingly, the object of the invention is to provide a physiological signal measurement apparatus, which can reduce the body moving interference generated in the measuring process.

In one aspect, the invention provides a physiological signal measurement method to improve the quality of the indirect-contact ECG signal measurement.

In order to achieve one or all of the above object, the invention provides a physiological signal measurement apparatus, which is capable of automatically adjusting a measure position and suitable for installed on a support element, and used to measure a physiological signal of a user. The physiological signal measurement apparatus includes a movable element, a physiological signal sensing element, a pressure sensing unit, and a microcontroller unit. The movable element has a first pressure inside thereof. The physiological signal sensing element is disposed on the surface of the movable element for sensing the physiological signal, the user exerts a second pressure on the physiological signal sensing element, and exerts a third pressure on the support element. The pressure sensing unit senses the first pressure, the second pressure and the third pressure to generate a pressure signal. The microcontroller unit is electrically connected to the physiological signal sensing element, the movable element and the pressure sensing unit, and for receiving the pressure signal sent from the pressure sensing unit and the physiological signal sent from the physiological signal sensing element. The microcontroller unit processes the pressure signal and the physiological signal with amplifying and filtering, controlling the movable element by means of the processed pressure signal and the physiological signal, in order to keep the physiological signal sensing element touching with the user.

In an embodiment, the physiological signal sensing element is a electrode for receiving the physiological signal of the user.

In another embodiment, the movable element adjusts the first pressure by expansion and contraction.

In another embodiment, the movable element is selected from one of an airbag and a spring.

In another embodiment, the physiological signal is selected from one of Electrocardiography (ECG) signal, photoplethysmogram (PPG) signal, body temperature and blood flow.

In another embodiment, the microcontroller unit has a signal processing circuit for amplifying and filtering the pressure signal sent from the pressure sensing unit and the physiological signal sent from the physiological signal sensing element.

In another embodiment, the physiological signal measurement apparatus further comprises an user interface, which is electrically connected to the microcontroller unit, for displaying an image showing the processed pressure signal and the physiological signal.

A physiological signal measurement method include the steps of: providing the physiological signal measurement apparatus said above; the user inputs a pressure setting value of the movable element by the user interface; the movable element adjusts a value of the first pressure to the pressure setting value; the pressure sensing unit senses the first pressure, the second pressure and the third pressure to generate the pressure signal; the physiological signal sensing element moves with the movable element, sensing the physiological signal of the user, and transmitting the physiological signal to the microcontroller unit; the microcontroller unit used to receive the pressure signal sent from the pressure sensing unit and the physiological signal sent from the physiological signal sensing element, the microcontroller unit processing the pressure signal and the physiological signal with amplifying and filtering, controlling the movable element by means of the processed pressure signal and the physiological signal, in order to keep the physiological signal sensing element in touch with the user.

In an embodiment, the physiological signal measurement method further comprises: the microcontroller unit transmits the processed pressure signal and the physiological signal to the user interface; the user interface displays an image showing the processed pressure signal and the physiological signal.

In another embodiment, the microcontroller unit controls the movable element by means of the processed pressure signal and the physiological signal comprises: the microcontroller unit sets a low pressure threshold and a high pressure threshold of the movable element; the microcontroller unit determines the value of the first pressure whether lower than the low pressure threshold; the movable element rise the first pressure to not lower than the pressure setting value if the value of the first pressure lower than the low pressure threshold.

In another embodiment, the physiological signal measurement method further comprises: when the microcontroller unit determines the value of the first pressure is greater than the low pressure threshold, then determines the value of the first pressure whether not lower than the high pressure threshold, if the value of the first pressure not lower than the high pressure threshold, the movable element reducing the first pressure to not greater than the pressure setting value, and repeats the step of determining the value of the first pressure whether lower than the low pressure threshold.

In another embodiment, the step of determining the value of the first pressure whether lower than the low pressure threshold comprises: the microcontroller unit determines the value of the second pressure whether lower than the low pressure threshold; the movable element rises the second pressure to not lower than the pressure setting value if the value of the second pressure lower than the low pressure threshold; the microcontroller unit determines the value of the second pressure whether not lower than the high pressure threshold, if the value of the second pressure not lower than the high pressure threshold, the movable element reduces the second pressure to not greater than the pressure setting value, and repeats the step of determining the value of the second pressure whether lower than the low pressure threshold.

In another embodiment, the physiological signal measurement method further comprises: the microcontroller unit starts or ends the measurement of physiological signal apparatus by means of the third pressure.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. In this regard, directional terminology, such as "top," "bottom," "front," "back," etc., is used with reference to the orientation of the FIGure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component facing "B" component directly or one or more additional components is between "A" component and "B" component. Also, the description of "A" component "adjacent to" "B" component herein may contain the situations that "A" component is directly "adjacent to" "B" component or one or more additional components is between "A" component and "B" component. Accordingly, the drawings and descriptions will be regarded as illustrative in nature and not as restrictive.

Figure 1:
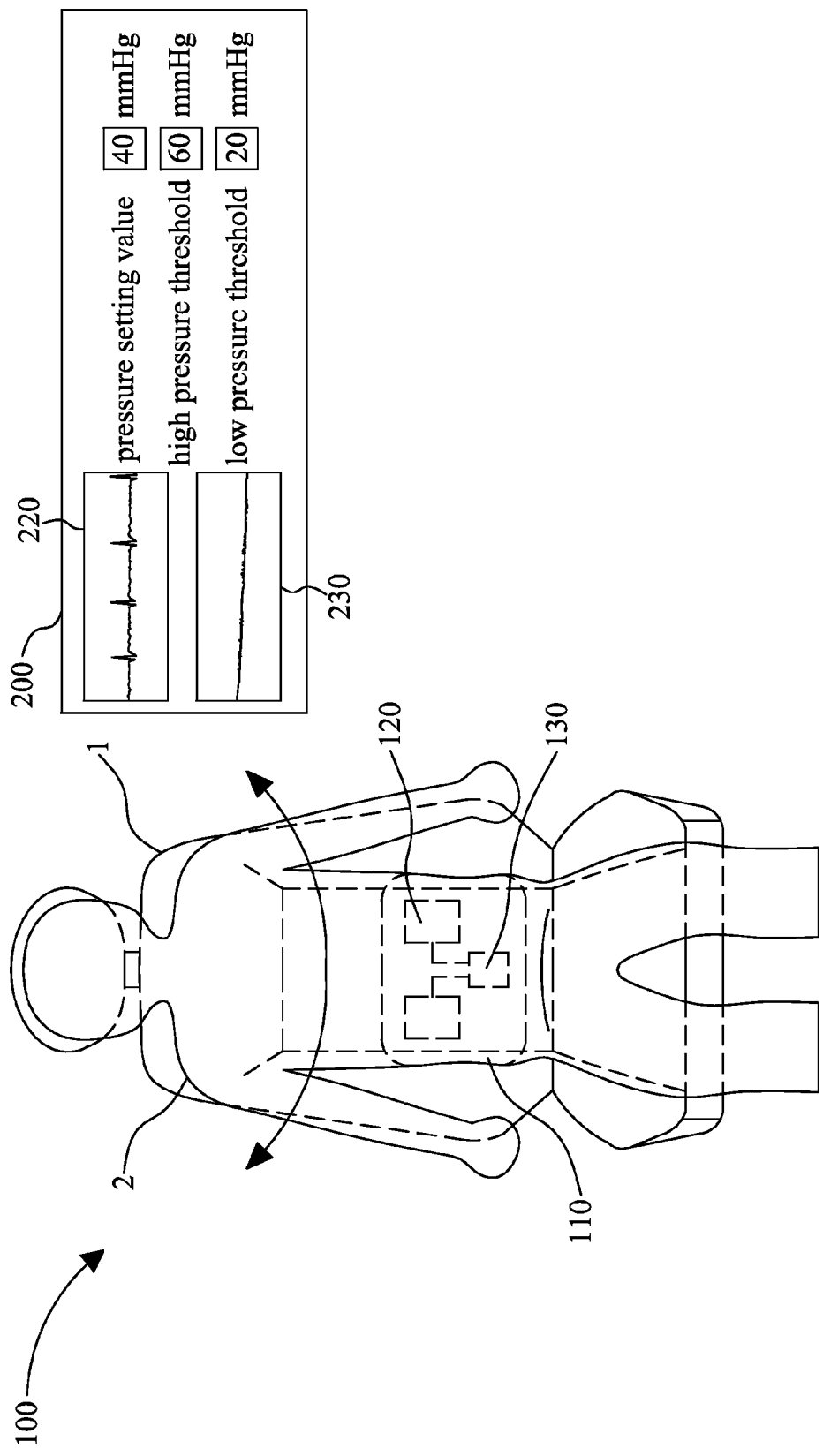
FIG. 1 is the physiological signal measurement apparatus.
Figure 5:
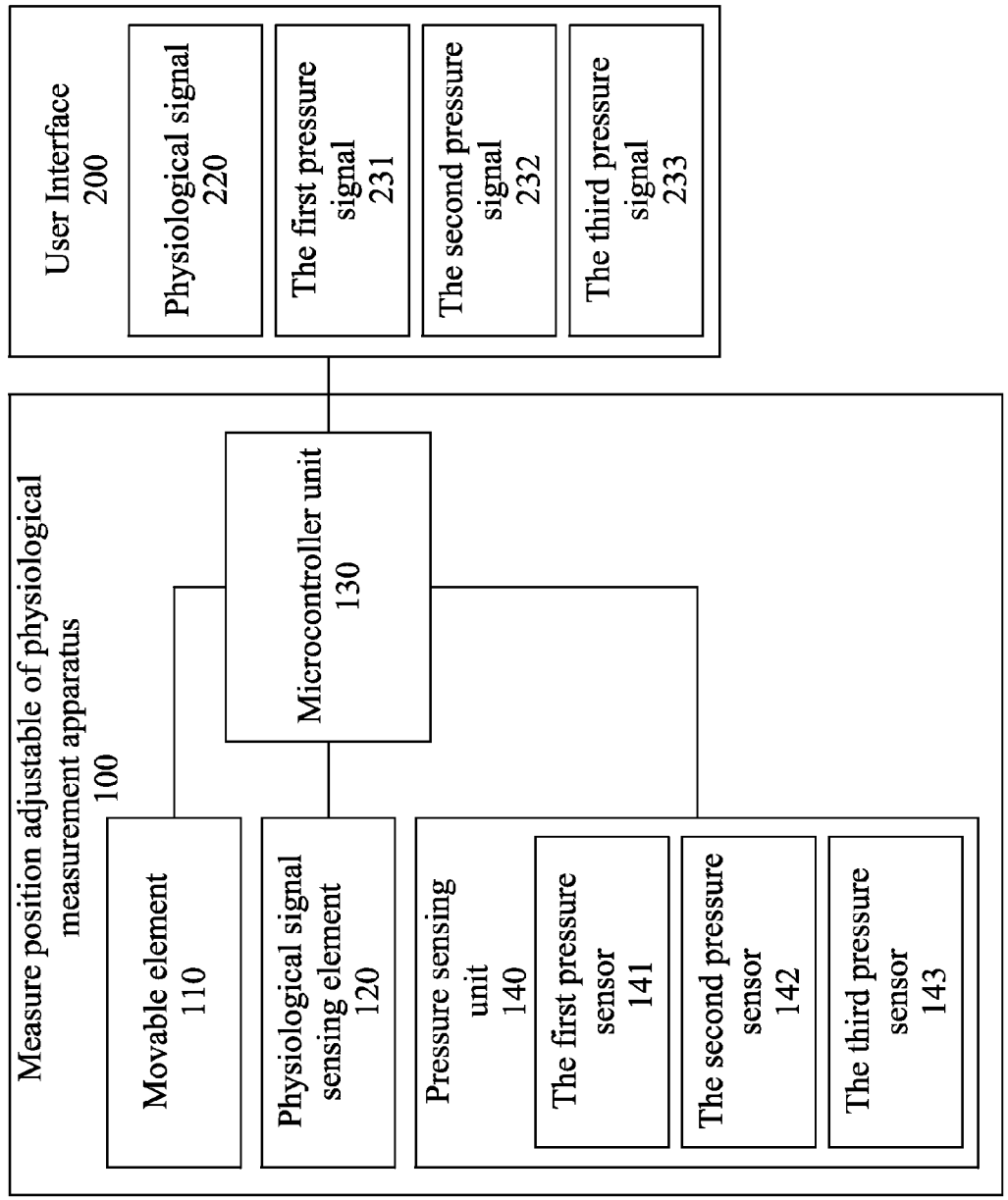
FIG. 5 is the hardware block diagram of the physiological signal measurement apparatus.

Refer to FIG. 1, it is the measure position adjustable of physiological signal measurement apparatus of the present invention 100. The physiological signal measurement apparatus 100 is capable of automatically adjusting a measure position thereof, and is installed on a support element, for example but not limited to a chair 1. The measure position adjustable of physiological signal measurement apparatus 100 is used to measure a physiological signal of an user 2, and includes a movable element 110, a physiological signal sensing element 120, a pressure sensing unit 140 (as shown in FIG. 5), and a microcontroller unit 130. The movable element 110 has a first pressure inside thereof. The physiological signal sensing element 120 is disposed on the surface of the movable element 110 and used to sense the physiological signal. The user 2 exerts a second pressure on the physiological signal sensing element 120, and exerts a third pressure on the chair 2. The pressure sensing unit 140 is electrically connected to the movable element 110 and the physiological signal sensing element 120. The pressure sensing unit 140 senses the first pressure, the second pressure and the third pressure to generate a pressure signal. The microcontroller unit 130 is electrically connected to the physiological signal sensing element 120, the movable element 110 and the pressure sensing unit 140. The microcontroller unit 130 is used to receive the pressure signal sent from the pressure sensing unit 140 and the physiological signal sent from the physiological signal sensing element 120. The microcontroller unit 130 processes the pressure signal and the physiological signal with amplifying and filtering. And the microcontroller unit 130 controls the movable element 110 by means of the processed pressure signal and the physiological signal, in order to keep the physiological signal sensing element 120 touching the user 2.

Continuing to refer to FIG. 1, the physiological signal measurement apparatus 100 further includes a user interface 200, which is electrically connected to the microcontroller unit 130, in order to be watched and controlled by the user 2. The microcontroller unit 130 processes the pressure signal and the physiological signal with amplifying and filtering, and transmits the processed signals to the user interface 200, then the user interface 200 displays an image showing the processed pressure signal and the physiological signal.

In an embodiment, the physiological signal sensing element 120 is a electrode, which is indirectly-contact to the user 2 and used to receive the physiological signal 121 of the user 2. The movable element 110 is an element which can expand and contract, for example but not limited to an airbag or a spring.

Figure 2:
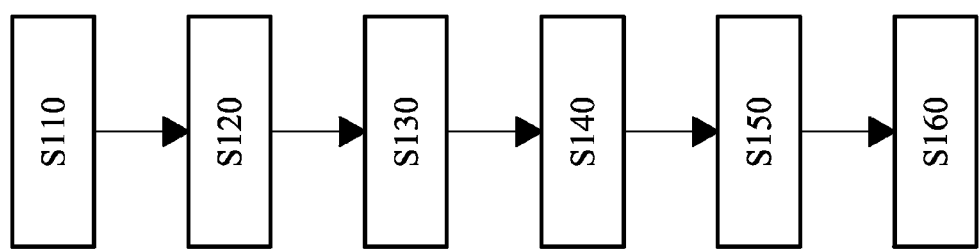
FIG. 2 is the flow chart of the physiological signal measurement method.

Refer to FIG. 2, which is the flow chart of a measure position adjustable of physiological signal measurement method. The physiological signal measurement apparatus 100 is used to perform the measure position adjustable of physiological signal measurement method. The physiological signal measurement method includes the following steps:

Step 110: The user 2 inputs a pressure setting value of the movable element 110 by the user interface 200, for example, 40 mm-Hg.

Step 120: The pressure sensing unit 140 senses the first pressure, the second pressure and the third pressure to generate the pressure signal.

Step 130: When the user 2 exerts the third pressure on the chair, the physiological signal measurement apparatus 100 starts to measure, and the movable element 110 adjusts the value of the first pressure to the pressure setting value.

Step 140: The physiological signal sensing element 120 moves with expansion and contraction of the movable element 110, and receives the physiological signal 121 of the user 2, and transmitting the physiological signal 121 to the microcontroller unit 130.

Step 150: The microcontroller unit 130 is used to receive the pressure signal sent from the pressure sensing unit 140 and the physiological signal sent from the physiological signal sensing element 120. The microcontroller unit 130 processes the pressure signal and the physiological signal with amplifying and filtering, and controls the expansion and contraction of the movable element 110 by means of the processed pressure signal and the physiological signal. In other words, the microcontroller unit 130 controls the movable element 110 inflated or deflated.

Step 160: The microcontroller unit 130 displays the image showing the processed pressure signals on the user interface 200.

Figure 3:
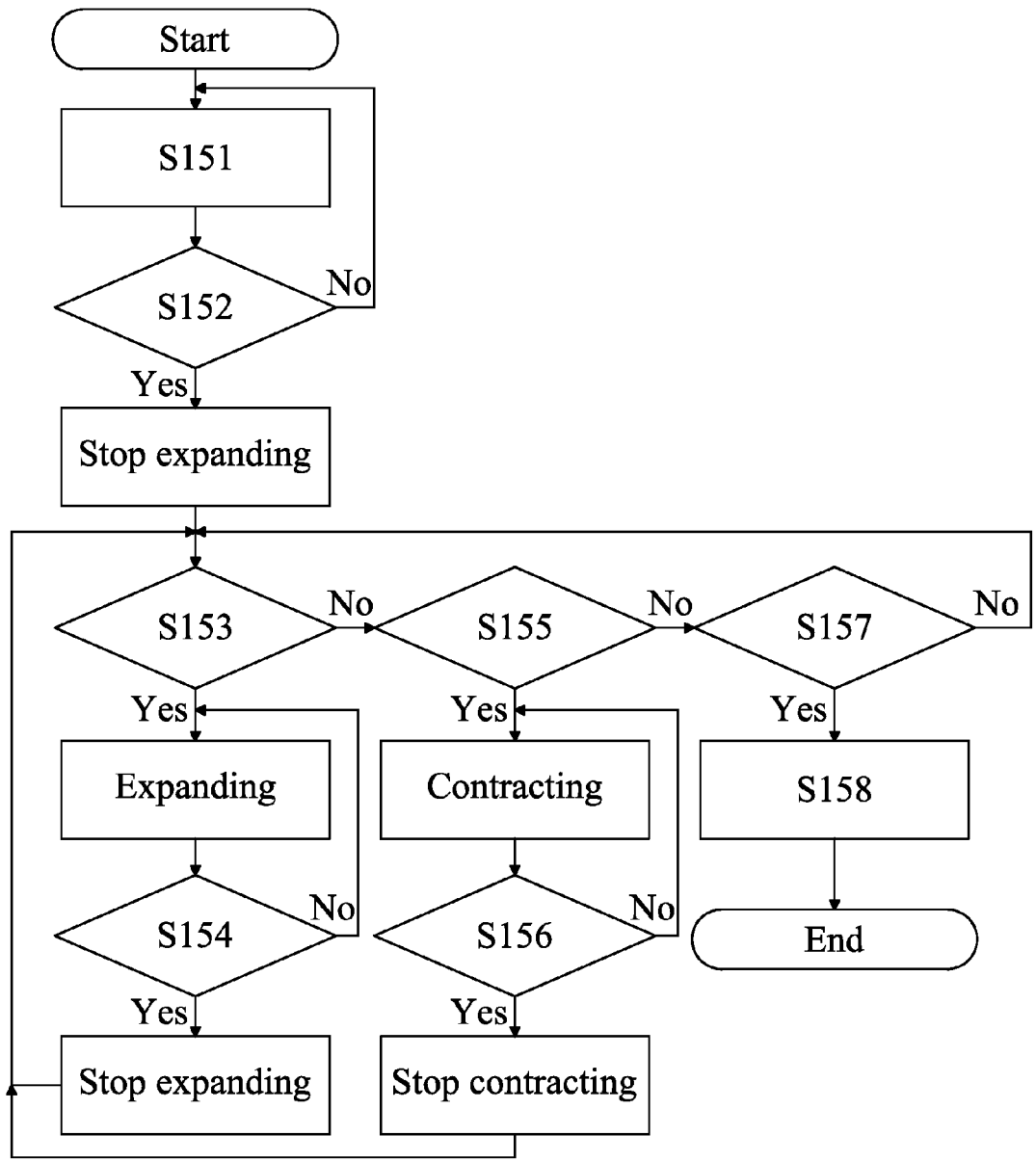
FIG. 3 is the flow chart of the step of the microcontroller unit 130 processes the pressure signal and the physiological signal with amplifying and filtering, and controlling the expansion and contraction of the movable element by means of the processed pressure signal and the physiological signal.

Refer to FIG. 3, which is the flow chart of the step 150 of the microcontroller unit 130 processes the pressure signal and the physiological signal with amplifying and filtering, and controls the expansion and contraction of the movable element 110 by means of the processed pressure signal and the physiological signal.

Step 151: The microcontroller unit 130 sets a low pressure threshold and a high pressure threshold of the movable element 110. The movable element 110 starts to expand, in order to make the first pressure equal to the pressure setting value, wherein the low pressure threshold is 20 mm-Hg and the high pressure threshold is 60 mm-Hg.

Step 152: The microcontroller unit 130 determines the value of the first pressure whether not lower than the low pressure threshold, if the decision is made "Yes", the movable element 110 stops expanding and to process Step 153. If the decision is made "No", then repeating the Step 151 to make the movable element 110 expand.

Step 153: The microcontroller unit 130 determines the value of the first pressure whether lower than the low pressure threshold, if the decision is made "Yes", the movable element 110 rise the first pressure to not lower than the pressure setting value and process Step 154. If the decision is made "No", then processing the Step 155.

Step 154: The microcontroller unit 130 determines the value of the first pressure whether not lower than the pressure setting value, if the decision is made "Yes", the movable element 110 stops expanding. If the decision is made "No", then the first pressure of the movable element 110 expands to not lower than the pressure setting value.

Step 155: The microcontroller unit 130 determines the value of the first pressure whether not lower than the high pressure threshold, if the decision is made "Yes", make the movable element 110 contract and process Step 156. If the decision is made "No", then process Step 157.

Step 156: The microcontroller unit 130 determines the value of the first pressure whether not greater than the pressure setting value, if the decision is made "Yes", the movable element 110 stops contracting. If the decision is made "No", then the first pressure of the movable element 110 contracts to not greater than the pressure setting value.

Step 157: The microcontroller unit 130 determines that the user 2 whether exits the chair, if the decision is made "Yes", then process Step 158. If the decision is made "No", then process Step 153 again.

Step 158: Ending the measurement of physiological signal, and make the movable element 110 contract. The Steps 151 to 158 can also control the expansion or contraction of the movable element 110 by means of the second pressure.

Figure 4:
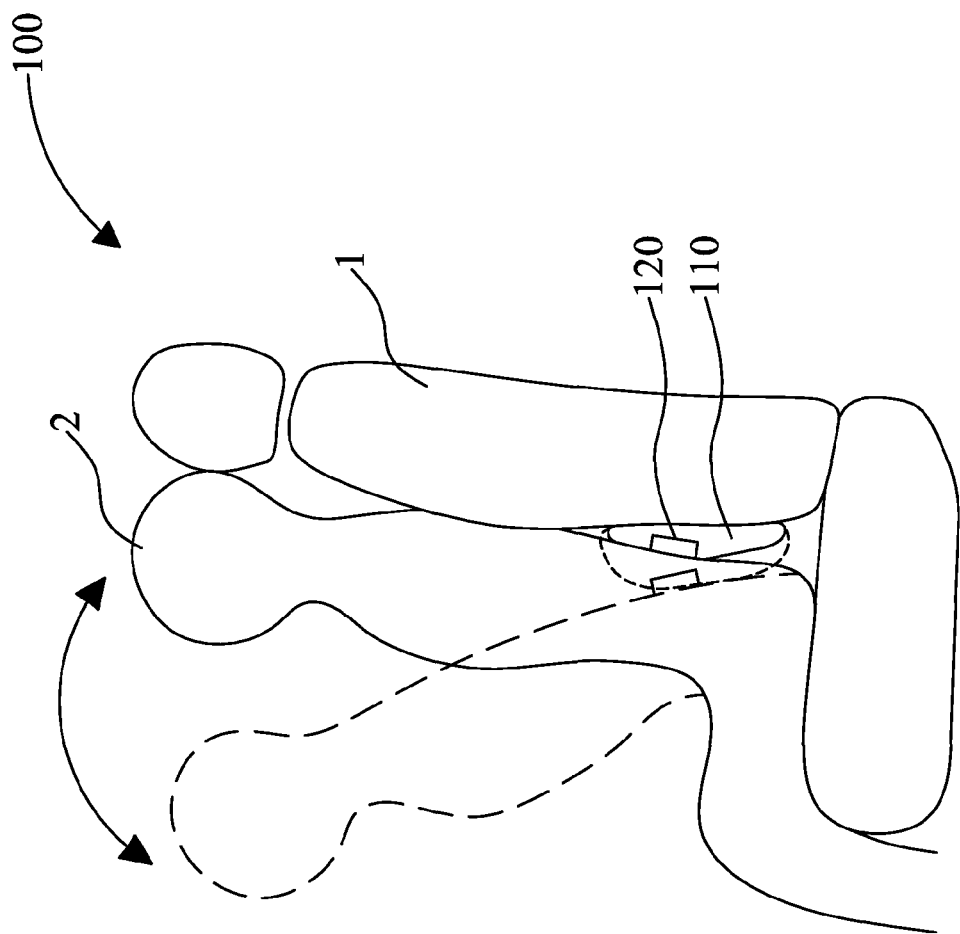
FIG. 4 is the change of the movable element.

Refer to FIG. 4, which shows the change of the movable element. When the user 2 moves away from the chair, the physiological signal sensing element 120 and the body of the user 2 getting farther away, and the first pressure of the movable element 110 declined. In this case, the microcontroller unit 130 controls the movable element 110 expanding to maintain the first pressure of the movable element 110, and to make the physiological signal sensing element 120 close to the user's body to maintain the physiological signal measurement without interference. Conversely, when the user 2 lies to the chair, the physiological signal sensing element 120 and the body are close to each other, and the first pressure of the movable element 110 is rising. In this case, the microcontroller unit 130 controls the movable element 110 contracting to reduce the first pressure of the movable element 110, so that user will not be discomfort because of the oppressive feeling. Refer to FIG. 1, when the user's body turns left and right, the movable element 110 changes with expansion or contraction to maintain the pressure of the movable element 110, and to make the physiological signal sensing element 120 maintain the physiological signal measurement without interference. In addition, it can also control the seat back to move forward and backward by sensing and adjusting the first pressure and the second pressure, to maintain the physiological signal sensing element 120 close to the user's body.

Refer to FIG. 5, which is the hardware block diagram of the measure position adjustable of physiological signal measurement apparatus. The movable element 110, the physiological signal sensing element 120, and the pressure sensing unit 140 are electrically connected to the microcontroller unit 130. The pressure sensing unit 140 includes a first pressure sensor 141, a second pressure sensor 142, and a third pressure sensor 143. The first pressure sensor 141 measures the pressure of the movable element 110, the second pressure sensor 142 measures the pressure of the movable element 110 exerted by the user, and a third pressure sensor 143 measures the pressure of the chair to determine whether the user sits on the chair. The first pressure sensor 141 provides a first pressure signal 231, the second pressure sensor 142 provides a second pressure signal 232, and the third pressure sensor 143 provides a third pressure signal 233. The microcontroller unit 130 amplifies and filters the signals, to display the image showing the processed signals on the user interface 200.

The present invention can be applied to car seats, aircraft seats or seat in general households, which changes the thinking that the electrode must install fixedly on the seat. The electrode can be automatically moved to adjust the optimum sensing position, in order to maintain the contact pressure between user and the electrode, and that the quality of ECG signal measurement is not affected by the interference generated by the moving of the body.

The foregoing description of the preferred embodiment of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the user matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A physiological signal measurement apparatus, capable of automatically adjusting a measure position and suitable for installed on a support element to measure a physiological signal of a user, the physiological signal measurement apparatus comprising:
   a movable element, having a first pressure inside thereof;
   a physiological signal sensing element, disposed on the surface of the movable element for sensing the physiological signal, the user exerting a second pressure on the physiological signal sensing element, and exerting a third pressure on the support element;
   a pressure sensing unit, electrically connected to the movable element and the physiological signal sensing element, for sensing the first pressure, the second pressure and the third pressure to generate a pressure signal; and
   a microcontroller unit, electrically connected to the physiological signal sensing element, the movable element and the pressure sensing unit, for receiving the pressure signal sent from the pressure sensing unit and the physiological signal sent from the physiological signal sensing element, wherein the microcontroller unit processes the pressure signal and the physiological signal with amplifying and filtering, and controls the movable element by means of the processed pressure signal and the physiological signal, in order to keep the physiological signal sensing element touching the user.

2. The physiological signal measurement apparatus of claim 1, wherein the physiological signal sensing element is a electrode for receiving the physiological signal of the user.

3. The physiological signal measurement apparatus of claim 1, wherein the movable element adjusts the first pressure by expansion and contraction.

4. The physiological signal measurement apparatus of claim 3, wherein the movable element is selected from one of an airbag and a spring.

5. The physiological signal measurement apparatus of claim 1, wherein the physiological signal is selected from one of Electrocardiography (ECG) signal, photoplethysmogram (PPG) signal, body temperature and blood flow.

6. The physiological signal measurement apparatus of claim 1, wherein the microcontroller unit has a signal processing circuit for amplifying and filtering the pressure signal sent from the pressure sensing unit and the physiological signal sent from the physiological signal sensing element.

7. The physiological signal measurement apparatus of claim 1, further comprising an user interface electrically connected to the microcontroller unit for displaying an image showing the processed pressure signal and the physiological signal.

* * * * *